US011234634B2

(12) United States Patent
Mischi et al.

(10) Patent No.: US 11,234,634 B2
(45) Date of Patent: Feb. 1, 2022

(54) TWO-DIMENSIONAL AND THREE-DIMENSIONAL STRAIN MAPPING FOR UTERINE CONTRACTIONS

(71) Applicant: TECHNISCHE UNIVERSITEIT EINDHOVEN, Eindhoven (NL)

(72) Inventors: Massimo Mischi, Eindhoven (NL); Benedictus Schoot, Eindhoven (NL)

(73) Assignee: TECHNISCHE UNIVERSITEIT EINDHOVEN, Eindhoven (NL)

( * ) Notice: Subject to any disclaimer, the term of this patent is extended or adjusted under 35 U.S.C. 154(b) by 33 days.

(21) Appl. No.: 16/647,678

(22) PCT Filed: Sep. 17, 2018

(86) PCT No.: PCT/EP2018/075039
§ 371 (c)(1),
(2) Date: Mar. 16, 2020

(87) PCT Pub. No.: WO2019/053249
PCT Pub. Date: Mar. 21, 2019

(65) Prior Publication Data
US 2020/0229754 A1 Jul. 23, 2020

(30) Foreign Application Priority Data
Sep. 15, 2017 (EP) .................................... 17191235

(51) Int. Cl.
*A61B 5/00* (2006.01)
*G06T 7/246* (2017.01)
(Continued)

(52) U.S. Cl.
CPC .............. *A61B 5/4356* (2013.01); *G06K 9/46* (2013.01); *G06T 7/0012* (2013.01); *G06T 7/246* (2017.01);
(Continued)

(58) Field of Classification Search
CPC ......... G06T 7/0012; G06T 7/20; G06T 7/246; G06T 7/70; G06T 7/73;
(Continued)

(56) References Cited

U.S. PATENT DOCUMENTS

| 2004/0210136 A1 | 10/2004 | Varghese et al. |
| 2009/0299212 A1* | 12/2009 | Principe et al. ..... A61B 5/1107 600/547 |
| 2014/0357996 A1 | 12/2014 | Miller et al. |

FOREIGN PATENT DOCUMENTS

| EP | 1772825 A1 | 4/2007 |
| WO | 2014080032 A1 | 5/2014 |

OTHER PUBLICATIONS

International Search Report and Written Opinion for PCT Patent App. No. PCT/EP2018/075039 (dated Nov. 23, 2018).
(Continued)

*Primary Examiner* — Andrew W Johns
(74) *Attorney, Agent, or Firm* — Kenealy Vaidya LLP (57) ABSTRACT

Some embodiments are directed to a method for quantitative visualization of uterine strain. The method includes receiving a number of 2D or 3D image frames acquired via an imaging technique and selecting a number of confidential points, determining the orientation of the uterus using the confidential points, selecting a region of interest, generating a grid of tracking points inside the region of interest and tracking and estimating the displacement of tracking points between frames. From a varying distance between each couple or set of tracking points, a strain is calculated. The orientation of the grid of tracking points and of the calculated strain is dependent on the determined orientation of the uterus.

19 Claims, 11 Drawing Sheets

(51) Int. Cl.
 *G06T 7/73* (2017.01)
 *G06K 9/46* (2006.01)
 *G06T 7/00* (2017.01)

(52) U.S. Cl.
 CPC ...... *G06T 7/73* (2017.01); *G06T 2207/10016* (2013.01); *G06T 2207/10136* (2013.01); *G06T 2207/20028* (2013.01); *G06T 2207/30004* (2013.01)

(58) Field of Classification Search
 CPC .......... G06T 2207/30004; A61B 5/033; A61B 5/1107; A61B 5/1128; A61B 5/5425; A61B 5/5436; A61B 8/08; A61B 8/485; A61B 8/5223
 See application file for complete search history.

(56) References Cited

OTHER PUBLICATIONS

Huang, Y., et al., "Quantitative Motion Analysis of the Uterus by Optical Flow and Two-dimensional Strain Mapping," 2018 IEEE International Symposium on Medical Measurements and Applications (MEMEA), IEEE, Jun. 11, 2018, pp. 1-5, XP033387777.

Mischi, M., et al., "Feasibility of uterine speckle tracking for improved embryo implantation," 2015 IEEE International Ultrasonics Symposium Proceedings (IUS), IEEE International, 2015, 4 pp.

Mischi, M., et al., "Quantitative ultrasound imaging of the uterus for improved embryo implantation: Preliminary study," 2015 IEEE International Conference on Digital Signal Processing (DSP), IEEE, Jul. 21, 2015, pp. 274-277, XP033199880.

A Kaur et al., "Transvaginal ultrasonography in first trimester of pregnancy and its comparison with transabdominal ultrasonography," J Pharm Bioallied Sci. Jul.-Sep. 2011; 3(3): 11 pages.

A Andersen et al., "Assisted reproductive technology in Europe, 2004: results generated from European registers by ESHRE," Human Reproduction vol. 23, No. 4, pp. 756-771, 2008.

G Whiteman-Elia et al., "A Primary Care Approach to the Infertile Couple," JABFP Jan.-Feb. 2001 vol. 14, No. 1, pp. 33-45.

G Mailloux et al., "Computer Analysis of Heart Motion from Two-Dimensional Echocardiograms," IEEE Transactions on Biomedical Engineering, vol. BME-34, No. 5, May 1987, pp. 356-364.

S Huang et al., "Analysis of Correlation Coefficient Filtering in Elasticity Imaging," IEEE Transactions on Ultrasonics, Ferroelectrics, and Frequency Control, vol. 55, No. 11, Nov. 2008, pp. 2426-2441.

N Kuijsters et al., "Uterine peristalsis and fertility: current knowledge and future perspectives: a review and meta-analysis," Elsevier, Reproductive Biomedicine Online 35 (2017) 50-71.

A Barjatya, "Block Matching Algorithms for Motion Estimation," DIP 6620 Spring 2004 Final Project Paper, Utah State University, pp. 1-6.

C Lam et al., "A New Cross-Diamond Search Algorithm for Fast Block Matching Motion Estimation," IEEE Int. Conf. Neural Networks & Signal Processing, Nanjing, China, Dec. 14-17, 2003, pp. 1262-1265.

J Vanne et al., "A High-Performance Sum of Absolute Difference Implementation for Motion Estimation," IEEE Transactions on Circuits and Systems for Video Technology, vol. 16, No. 7, Jul. 2006, pp. 876-883.

S Zhu, et al., "A New Diamond Search Algorithm for Fast Block-Matching Motion Estimation," IEEE Transactions on Image Processing, vol. 9, No. 2, Feb. 2000, pp. 287-290.

M Ijland, et al., "Velocity of endometrial wavelike activity in spontaneous cycles," American Society for Reproductive Medicine, Elsevier Science Inc., Fertility and Sterility, vol. 68, No. 1, Jul. 1997, pp. 72-75.

Ml Ijland, et al., "Endometrial wave direction switch and the outcome of in vitro fertilization," American Society for Reproductive Medicine, Elsevier Science Inc., Fertility and Sterility, vol. 71, No. 3, Mar. 1999, pp. 476-481.

S Novellas, et al., "MRI Characteristics of the Uterine Junctional Zone: From Normal to the Diagnosis of Adenomyosis," AJR Women's Imaging:196, May 2011, 12 pages.

R Fanchin, et al., "Uterine contractions at the time of embryo transfer alter pregnancy rates after in-vitro fertilization," Human Reproduction vol. 13, No. 7, pp. 1968-1974, 1998.

R Fanchin, et al., "Uterine dynamics: impact on the human reproduction process," RBMOnline—vol. 18. Suppl.2 2009 57-62 Reproductive BioMedicine Online; www.rbmonline.com/Article/3811 on web Jan. 26, 2009.

R Lopata, et al., "Dynamic imaging of skeletal muscle contraction in three orthogonal directions," Innovative Methodology, J Appl Physiol 109: 906-915, 2010.

T Kawagishi, "Speckle Tracking for Assessment of Cardiac Motion and Dyssynchrony," Echocardiography: A Jrnl. of CV Ultrasound & Allied Tech., vol. 25, No. 10, 2008, pp. 1167-1171.

\* cited by examiner

TWO-DIMENSIONAL AND THREE-DIMENSIONAL STRAIN MAPPING FOR UTERINE CONTRACTIONS

CROSS REFERENCE TO RELATED APPLICATIONS

This application is a national phase filing under 35 C.F.R. § 371 of and claims priority to PCT Patent Application No. PCT/EP2018/075039, filed on Sep. 17, 2018, which claims the priority benefit under 35 U.S.C. § 119 of European Patent Application No. 17191235.5, filed on Sep. 15, 2017, the contents of each of which are hereby incorporated in their entireties by reference.

BACKGROUND

Some embodiments of the presently disclosed subject matter relate to a system and method for quantitative visualization of uterine strain, and to a computer readable medium for performing such a method on a computer.

Nowadays, up to 20% of couples have difficulties in giving birth by themselves [1]. The hope of all or most of these ill-fated couples relies on assisted reproductive technology. The In-Vitro Fertilization (IVF) is the most advanced technique, but the effectiveness per treatment cycle remains below 30% [2]. Uterine contractions are considered as a major involvement causing IVF failure [3], [4], [5].

They have been so far investigated by many invasive techniques, such as, intrauterine pressure catheter, magnetic resonance imaging (MRI), and hysterosalpingoscintigraphy [1]. Transvaginal ultrasound (TVUS) is treated as an effective, invasive and safe approach for the measurement of uterine peristalsis (UP). At the present, just qualitative evaluation of UP has been performed. However, the interpretation of UP based on ultrasound (US) video loops is also difficult and subjective even for experienced sonographers [2].

Nevertheless, the development and improvement of motion tracking has already built a good platform in the field of medical imaging, such as cardiovascular [6] and muscular analysis [7]. The backscattered ultrasound waves form a deterministic intensity patterns due to their constructive/destructive interference which is referred to as speckle pattern. The speckle pattern moves along with tissue across consecutive frames, allowing for visualization of tissue motion.

SUMMARY

One aspect of some embodiments of the presently disclosed subject matter therefore is to improve the methods of the related art.

Accordingly, some embodiments provide a method for quantitative visualization of uterine strain, the method including:
  receiving a number of 2D or 3D image frames acquired via an imaging technique;
  selecting a number of confidential points;
  determining the orientation of the uterine using the confidential points;
  selecting a region of interest;
  generating a grid of tracking points inside the region of interest;
  tracking and estimating the displacement of tracking points between frames;
  calculating, from a varying distance between each couple or set of tracking points, at least one of:
    a transversal strain,
    a longitudinal strain,
    a circular strain,
    an area strain and
    a volume strain,
  to obtain a strain map, wherein the orientation of the grid of tracking points and of the calculated strain is dependent on the determined orientation of the uterus.

Some embodiments are defined in the dependent claims.

Applications can be various, ranging from the context of in-vitro fertilization, looking for a quiet period that is suitable for embryo transfer, up to menstrual pain, with the aim of understanding the muscular implications.

In some embodiments the method further includes:
  visualizing the 2D or 3D image frames with their corresponding strain map as an overlay.

In some embodiments the method further includes:
  rendering the obtained strain map with a predefined color map to present a coloured strain map for each frame in time;
  visualizing the 2D or 3D image frames with the coloured strain maps as an overlay.

In some embodiments, a bull eye plot is used to visualize 3D strain where the center of the plot represents strain in the cervix and the outer ring represents strain in the fundus or vice versa.

In some embodiments, the area strain is determined based on the changes in the areas determined by sets of 3 or more tracked points, where the points can be positioned relative to the uterine anatomy.

In some embodiments, the volume strain is determined based on the changes in the areas determined by sets of 4 or more tracked points, where the points can be positioned relative to the uterine anatomy.

In some embodiments, the tracking includes optical flow techniques.

In some embodiments, the tracking includes block matching. To this end, blocks at different frames are matched by minimizing (or maximizing) a cost function such as the mean squared error, the sum of absolute errors, or the mutual information.

Robustness can be increased by several techniques introducing either averaging or median filtering. A fast search method can be used to replace a full or multiscale search. A diamond search is an option that permits accelerating the analysis by over 70%. Although we are dealing with small strains, strain compensation can be introduced to compensate for deformation within the block.

In some embodiments, the block matching includes:
  preprocessing of the images by regularization, filtering, or decomposition methods;
  defining one or more blocks in a frame;
  defining a similarity measure, such as normalized correlation, mutual information, or sum of absolute errors;
  searching for the most similar blocks in the following frame;
  using smart search algorithms, such as a diamond search;
  combining the displacement estimates from neighboring blocks, using median or average filters;
  summing the estimated displacements over time;
  post processing, such as moving average filtering.

In some embodiments, the strain directions are relative to the endometrial long axis and presented in radial, longitudinal, and circular directions.

In some embodiments, the strain directions are relative to the outer contour of the uterus or the endometrium, and presented in radial, longitudinal, and circular directions.

In some embodiments, the calculated strain map is projected on one or more 2D images for presentation purposes.

In some embodiments, the presented dynamic map of strain is accelerated for visualization purposes.

In some embodiments, a global uterine activity parameter is provided for quantification of the strain amplitude, strain direction, and/or frequency spectrum of the strain.

In some embodiments, contractions in the uterus are counted based on changes in either direction or amplitude of strain, or both.

In some embodiments, the method includes calculating a propagation velocity and direction of the uterine contractions relative to the orientation of the uterus using the measured contractions. This can be derived by analysis of the temporal and spatial frequency representation of the contractions relative to the orientation of the uterus. Alternative approaches rely on the measurement of strain delays between different points aligned according to the uterine orientation.

In some embodiments, the step of selecting a number of confidential points includes receiving orientation information on the orientation and/or outline of the uterus from a user.

In some embodiments, the imaging technique is an ultrasound imaging technique, and the frames can include or can consist of either a set of Radio-frequency lines or demodulated gray-level images.

According to some other embodiments, a system is provided for quantitative visualization of uterine strain, the system including a computer having a processor and an interface, the interface being configured to receive measurement data from a measuring device, wherein the processor is configured to perform the method as described above.

The presently disclosed subject matter also relates to a computer readable medium for storing a computer program including instructions which, when executed by a computer, cause the computer to perform the method as described above.

BRIEF DESCRIPTION OF THE DRAWINGS

These and other aspects of some embodiments of the presently disclosed subject matter are apparent from and will be elucidated with reference to some embodiments described hereinafter. In the drawings.

It should be noted that items which have the same reference numbers in different Figures, have the same structural features and the same functions, or are the same signals. Where the function and/or structure of such an item has been explained, there is no necessity for repeated explanation thereof in the detailed description.

DETAILED DESCRIPTION OF EXEMPLARY EMBODIMENTS

Below, some exemplary embodiments of the presently disclosed subject matter will be described. The specific numbers and dimensions mentioned below are not meant to be restrictive, and are used to explain some embodiments of the presently disclosed subject matter.

A. Ultrasound Acquisition

In a pilot study, US acquisitions were performed at the Catharina Hospital, Eindhoven (The Netherlands) with a WS80A (Samsung-Medison) US scanner equipped with a transvaginal E5-9 (3D) probe. In vivo, 4-minute TVUS scans were performed. Six women with no infertility problems attending the gynecology department at the Catharina Hospital, Eindhoven (The Netherlands) were involved in this study. For each woman, two scans were performed during the late follicular (LF) and late luteal (LL) phase of the menstrual cycle. In the pilot study, 2D TVUS recordings were chosen as test targets. The acquisition frame rate for the 2D TVUS recording was 30 frames/s.

B. Image Preprocessing

Each image in the acquired recording may be preprocessed to regularize the spatial resolution by Wiener deconvolution filtering as proposed in [9]. The resulting image presents an isotropic resolution with speckle size of e.g. 1 mm. Due to the high frame rate (30 Hz) compared to the slow myometrial movement 2 mm/s [10], the movement between two frames is limited [11]. Therefore, each image may be up-sampled by a factor of 2 to increase the tracking resolution. For example, each up-sampled image had 1360 by 2180 pixels. Additional preprocessing steps may also be considered with the aim of removing clutter noise and enhancing the signal coming from moving uterine structures. To this end, singular value decomposition or principal component analysis can be considered.

C. ROI Positioning

Figure 1A:
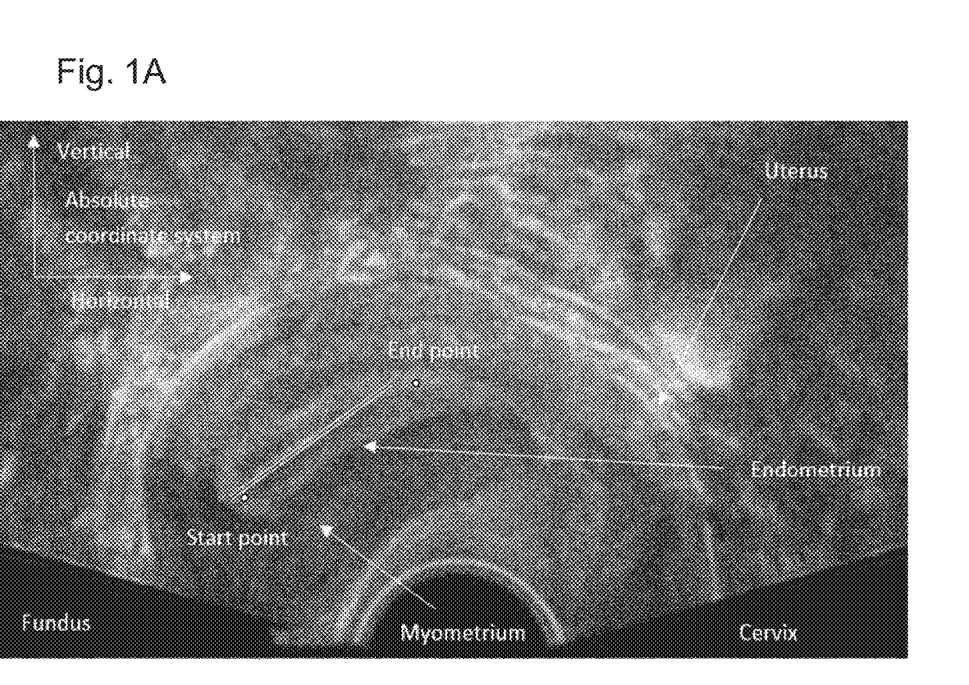
FIG. 1A shows an example of a line drawing along the endometrium on the first frame, relative to the LF phase of a particular patient.

FIG. 1A shows a first frame of the TVUS recording of the uterus, relative to the LF phase of a particular patient. Due to the probe position during the acquisition of the TVUS video loop, the uterus is not laid in the horizontal direction. It is difficult to choose a suitable, rectangular ROI if the uterus is rotated by a certain angle compared to the absolute coordinate system, relative to the US image. To solve this problem, a line along the endometrium cavity, referred to as the endometrium line with a start point and an end point, can be first drawn by the user, see FIG. 1A. In this case, the start point and end point function as the confidential points. Then, the image rotates based on the angle between the drawn line and the horizontal direction of the US image to make sure that the border of the endometrium is in line with the absolute coordinate system. In this case, a ROI could be easily drawn with a draggable rectangle around the endometrium on the rotated frame, covering the junctional zone around the fundus. Now a grid of points, also referred to as dots-map, can be generated inside the rectangular ROI with 30-pixel-space between two dots in both directions, see FIG. 1B. This space assured that the two blocks centered around the adjacent two dots will not overlap each other. It should be noted that different distances (larger or smaller) between dots are possible, also depending on the resolution of the images. The coordinates of these dots in the rotated frame may be multiplied by a rotation matrix to obtain the corresponding coordinates in the absolute horizontal and vertical direction.

D. Speckle Tracking

Two types of speckle tracking may be used and will be described below. These two types are endometrium line tracking and ROI tracking.

Figure 2:
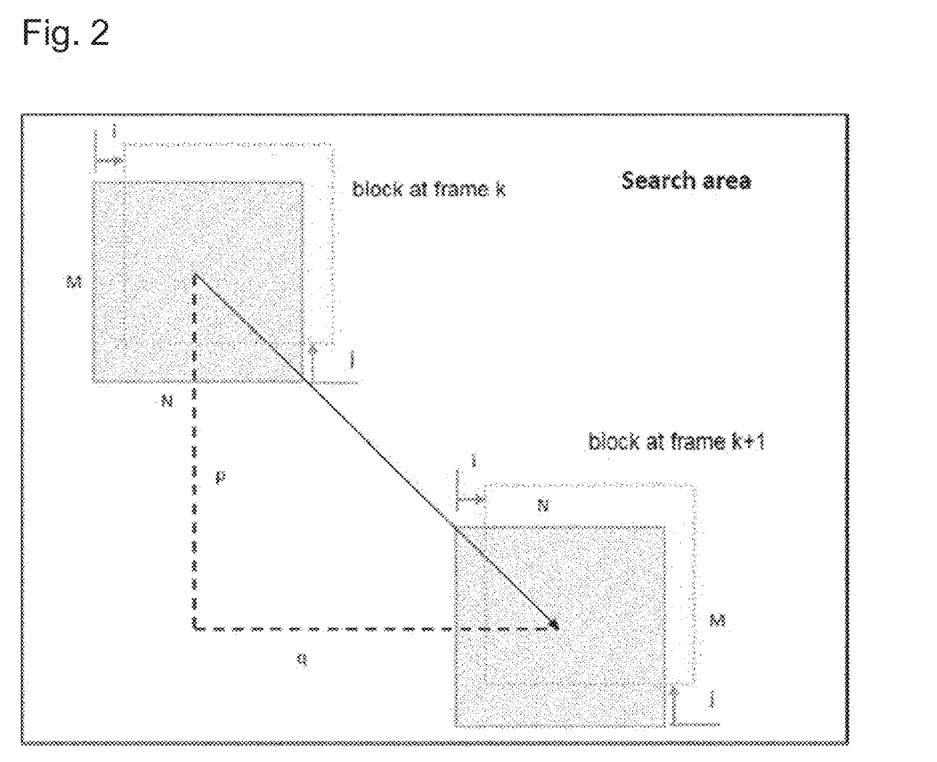
FIG. 2 shows a diagram to explain block matching within a predefined search area.

1) Endometrium Line Tracking:

In reality, the endometrium does not hold in a fixed location due to the probe manipulation and the global movement of the myometrium. To make sure that the dots-map can follow and cover the same part of the endometrium chosen in the first frame, a fast block matching algorithm based on the Sum of Absolute Difference (SAD) error metrics [13], accelerated by a Diamond Search method (DS) may be applied to the start and end points of the endometrium line. The principle of block matching is to choose an N×M block in the reference frame and then search for its new position in the next frame by minimizing a cost function (error metrics) within the entire predefined search area, see FIG. 2. The search area can be defined based on the maximum expected tissue displacement between two subsequent frames. The position where the highest similarity (HS) is found is then considered as the best or better match. This process may be applied frame by frame through the whole video recording. The robustness of the method can be improved by combining (mean or median) the results from neighboring blocks [19]. A good compromise between robustness and speed is taking just the first neighboring block in each direction (9 blocks in total). Traditional block matching uses a grid full-search method (FS) which evaluates all or most the possible positions of the matching block inside the search area. The disadvantage of performing a FS is its high computation time [14]. To overcome this problem while preserving good tracking accuracy, DS was found as one possible fast-search method for block matching in TVUS recordings.

Figure 3A:
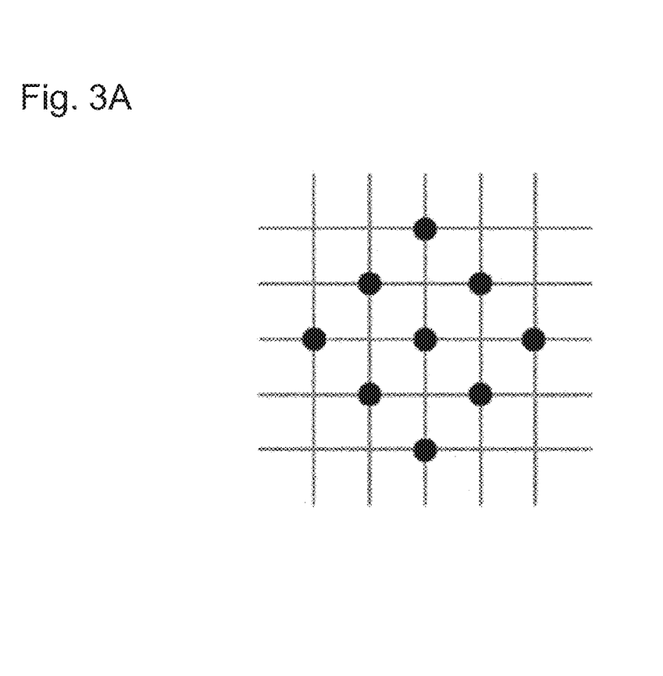
FIG. 3A shows a large-diamond search pattern.
Figure 3B:
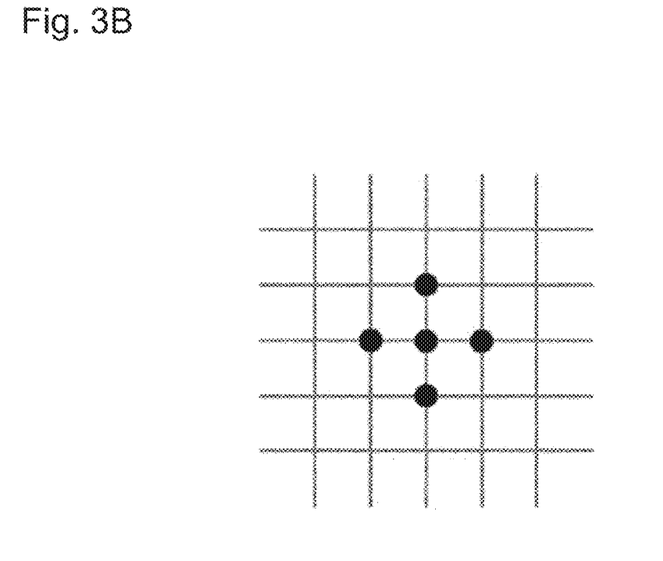
FIG. 3B shows a small-diamond search pattern.

Instead of evaluating the similarity between the reference and the matching blocks over the whole search area, DS has its own search pattern [15], [16]. DS first starts the evaluation based on a large diamond search pattern (LDSP) process (FIG. 3a). If the center block has the HS among substantially all the nine blocks, other four blocks surrounding the center will be evaluated, which is known as small diamond search pattern (SDSP) process (FIG. 3b). The best or better match is then treated at the position with the HS among the center block and the four surrounding blocks. If the center block does not have the HS, the position with the HS will be set to the new center for the LDSP. This step can be repeated until the HS belongs to the center block, and then the best or better match will be found through the result of the SDSP process. Since the block's movement between two frames is limited, the best or better match may be found only in few iterations so that the number of evaluations is largely reduced compared to FS. In previous study, SAD with DS saved up to 80% of the computation time preserving the same tracking quality compared to the FS.

Next to the use of block matching, speckle tracking can also make use of optical flow concepts, solving a first order approximation of the image intensity variations due to motion [20]. In practice, due to poor signal-to-noise ratios or signal decorrelation between frames (out of plane motion), the tracking results may be less accurate. Therefore, moving average (MA) filters with different window lengths were also tested to post-process the estimated displacement signals.

Tracking the endometrial line is performed in order to create an anatomical reference for calculating and displaying uterine motion. With this method, the following ROI and dots-map can refer to the same part and orientation of the myometrium according to the choice made by the operator. Moreover, the estimates can refer to the uterine anatomy, providing strain values that have a physiological meaning, irrespective of the changing rotation and orientation of the uterus. Next to the endometrial line, a good reference for uterine orientation and rotation can also be provided by the outer contour of the uterus or the endometrium, which is also visible in the images.

2) ROI Tracking:

After acquiring the optimal dots-map locations in each frame, speckle tracking may be applied again to these dots in order to track the UP. Due to the influence of out-of-plane motion of the uterus, small changes in the interference pattern can occur and the gray value of the image could largely change between two adjacent frames. This phenomenon leads to changes in the speckle pattern across subsequent frames. As a consequence, the block matching might find an incorrect position as the best or better match, causing an off-track problem. Once an off-track occurs, the tracking error will propagate and accumulate through the full recording. To overcome this problem, a modified speckle tracking algorithm may be applied. Instead of shifting blocks to their best or better matching positions, the changes in position, which are the shifts of the blocks between two subsequent frames, are saved, while the position of the blocks are set back to the original dots-map locations relative to the tracked endometrial line. In other words, the speckle tracking may only be applied between two adjacent frames and does not influence the remaining frames. This way, any tracking error will not propagate and accumulate throughout the frames.

E. Propagation Reconstruction

The simplest way of translating shifts into movements is applying the cumulative sum method. This can be implemented by a moving sum. The moving sum method performs a local k-point sum, where each sum is calculated over a sliding window of length k across neighboring elements of the original signal. It is realized by calculating the convolution between the shifts of a single block over the whole recording and a 1-s rectangular function of length k and amplitude 1.

Another benefit of applying a moving sum is in the possibility to tune the method to specific frequencies. The uterine contraction rate based on the literature [17] is 3-5 contractions per minute for a healthy woman during the LF phase and 0-2 contractions per minute during the LL phase. Based on these frequency ranges, in this pilot study we have considered an average value of 3 contractions per minute, corresponding to 600 frames per cycle. In order to reconstruct such a frequency, the window length k should be chosen to be smaller than half of the contraction cycle. The tracking results are the shifts in the horizontal and vertical directions of substantially all the blocks processed by the algorithm; however in reality the UP occurs in transversal and longitudinal directions relative to the endometrial line. A rotation matrix with the angle acquired from the endometrium line tracking in each frame was then multiplied by the tracking results to project these shifts into the transversal and longitudinal directions of the uterus. The moving sum method may be applied to the transformed shifts to reconstruct the movement of each dot at the desired frequency in each direction. After the reconstruction, the inverse rotation matrix was multiplied by the reconstructed movements to bring them back to the absolute horizontal and vertical coordinates.

F. Strain Calculation

Figure 1B:
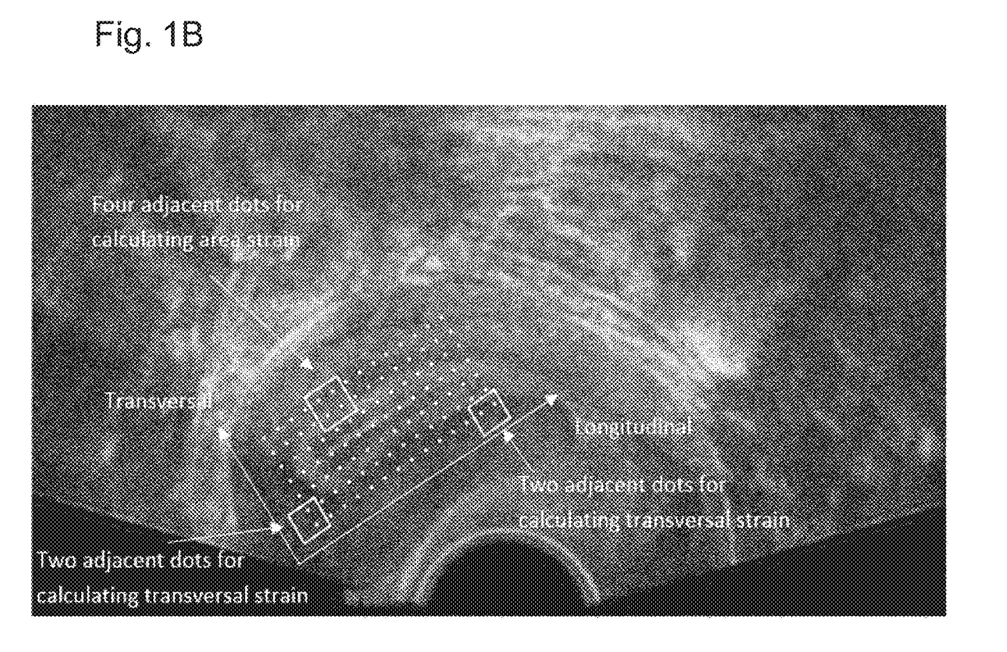
FIG. 1B shows a dots-map created in the ROI, based on the drawn line in FIG. 1A.

In this study, the Lagrangian strain was calculated in two ways. According to Eq. 1, the strain was calculated as the relative change in the distance, $D(t)-D(t_0)$, between two dots in either transversal or longitudinal direction divided by their original distance, $D(t_0)$, frame by frame. According to Eq. 2, the strain, considered as the area strain, was calculated as the relative change in the area, $A(t)-A(t_0)$, divided by their original area, $A(t_0)$. The area is based on four adjacent dots in the ROI (FIG. 1B).

$$\text{Strain}=(D(t)-D(t_0))/D(t_0) \quad (1)$$

$$\text{Area Strain}=(A(t)-A(t_0))/A(t_0) \quad (2)$$

Since the area strain takes into consideration the changes in both directions, the results are expected to be easier to interpret compared to one-dimensional strain.

G. Interpolation and Colour Coding

Figure 4:
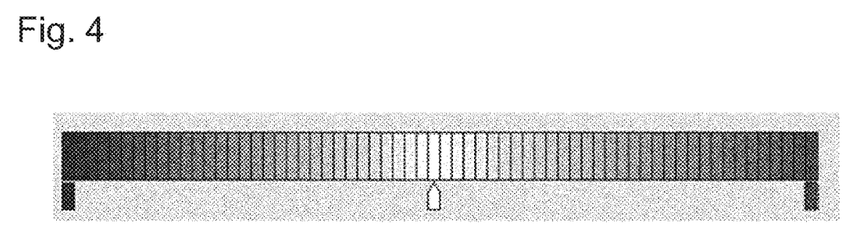
FIG. 4 shows an example of a colour map for colour coding.

The strain results acquired from the previous step were just between two dots or among four dots. To create a colour map covering the whole ROI, each pixel in the ROI should have its own value. Bicubic interpolation may therefore be applied to interpolate the strain results and cover the entire ROI in a smooth way. It is noted that other interpolation techniques are possible. The visualization step may be achieved by applying colour coding to the interpolation results. A colour map with 65 different colours can be defined to represent the strain values varying from −50% to 50% (FIG. 4). If the strain result is out of this range, it will be coded with the same colour as 50% or −50% correspondingly. For example, the negative strain can be divided into 32 gradient blue colours, revealing the degree of the uterine contraction. The positive strain can be coded in e.g. 32 gradient red colours to achieve the same effect but representing the uterine relaxation. If the strain is zero, which means no deformation, it will show white.

Results

A. Endometrium Line Tracking

Figure 5:
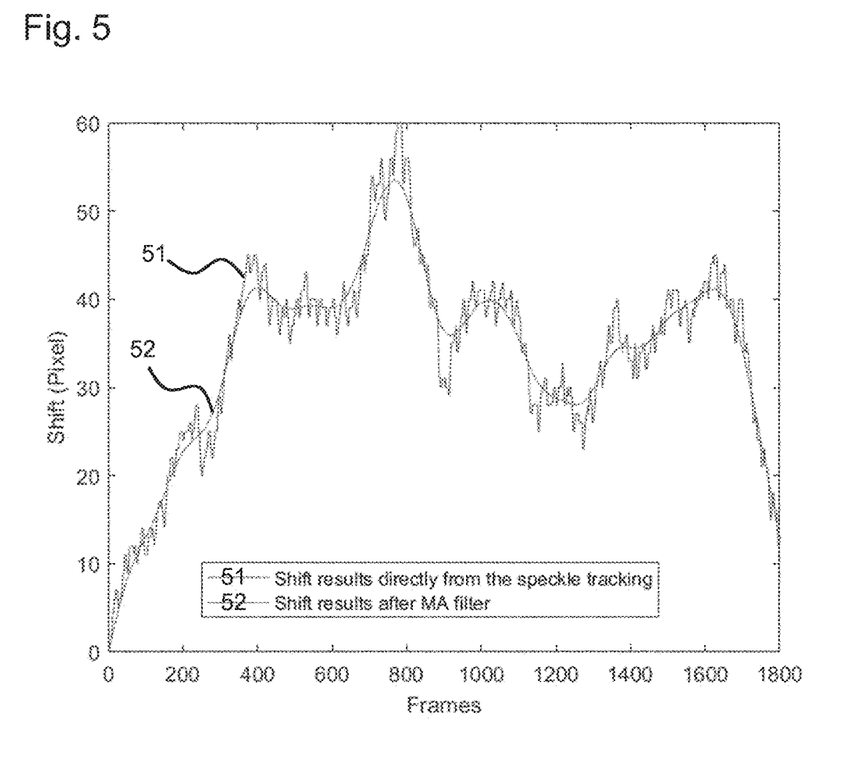
FIG. 5 is an example of the shift curve corresponding to the start point of the endometrium line in horizontal direction through a 2-minute TVUS recording, relative to the LF phase of the particular patient.

The endometrium line tracking may be achieved by applying the fast block matching algorithm based on SAD and DS on the start and end point of the endometrium line. After applying cumulative sum to the tracking result, a continuous shift curve (trajectory) can be constructed. An MA filter may be applied to the estimated displacements to smooth the estimated trajectory of both points. The choice of the window length of the MA filter was tested from 30 frames to 300 frames. A window length of 90 frames gave the optimal performance, FIG. 5.

B. Propagation Reconstruction

The speckle tracking analysis for the ROI tracking was different from the endometrium line tracking as it calculates the strain at locations (points) that are fixed relative to the uterine anatomy. A moving sum method is therefore more suited than a cumulative sum to reconstruct the shift curve. With multiple tests, the optimal window length, k, was finally decided as 150 frames which is one fourth of the contraction cycle.

Figure 6A:
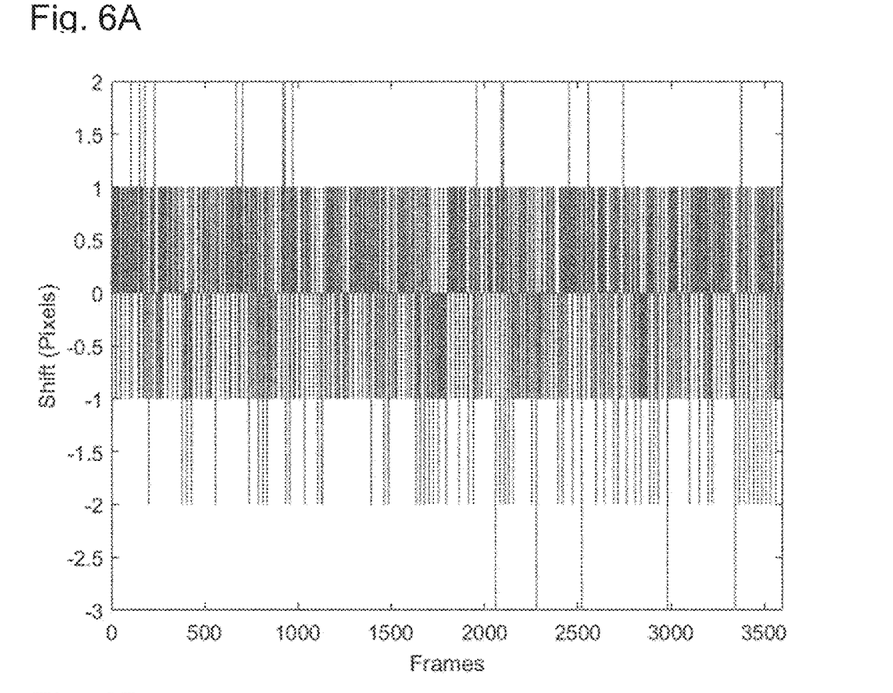
FIG. 6A shows an example of speckle tracking result of a single dot in horizontal direction from modified speckle tracking algorithm, relative to the LF phase of the particular patient.
Figure 6B:
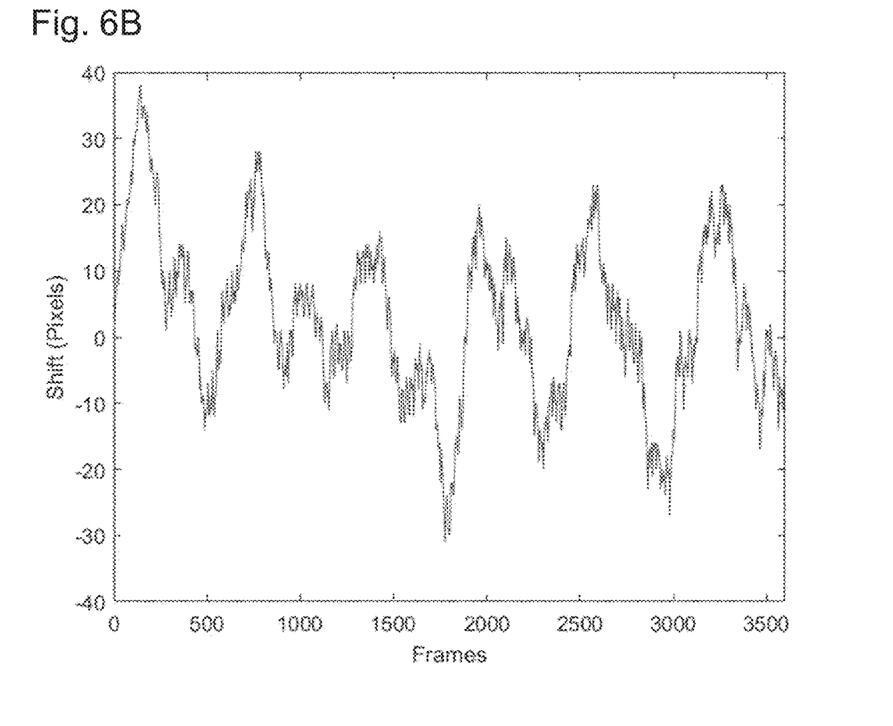
FIG. 6B shows a reconstructed shift curve after applying the moving sum method to the tracking result.

The tracking results of a single dot (Row 2 Column 5 in the map) in transversal direction through a 2-minute TVUS recording is shown in FIG. 6A and the reconstructed shift curve based on the moving sum method is depicted in FIG. 6B.

Figure 6C:
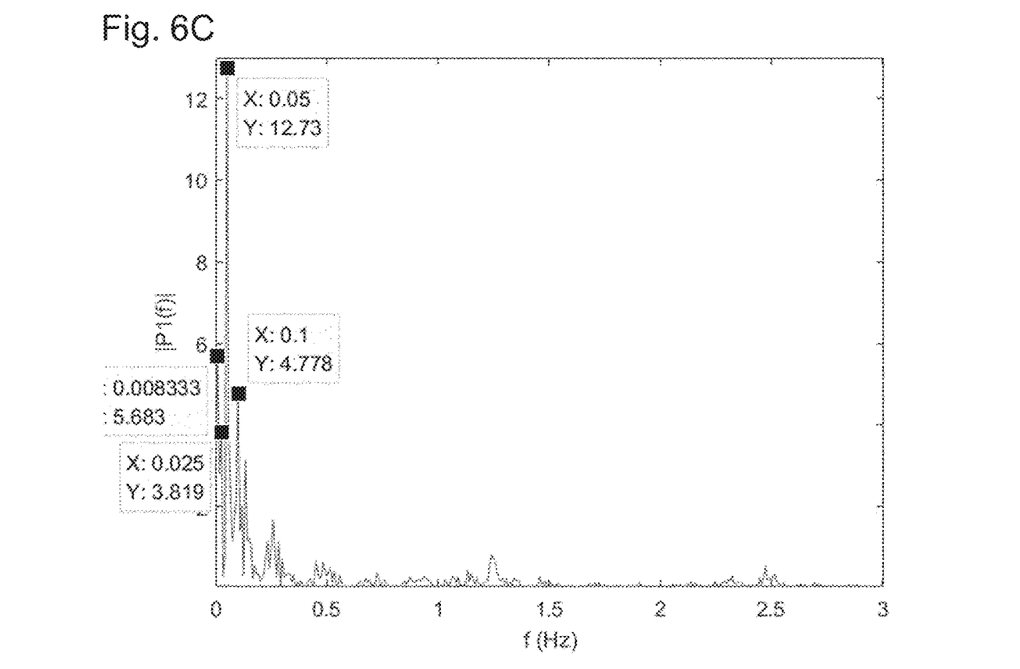
FIG. 6C shows a frequency spectrum of the reconstructed shift curve.
Figure 6D:
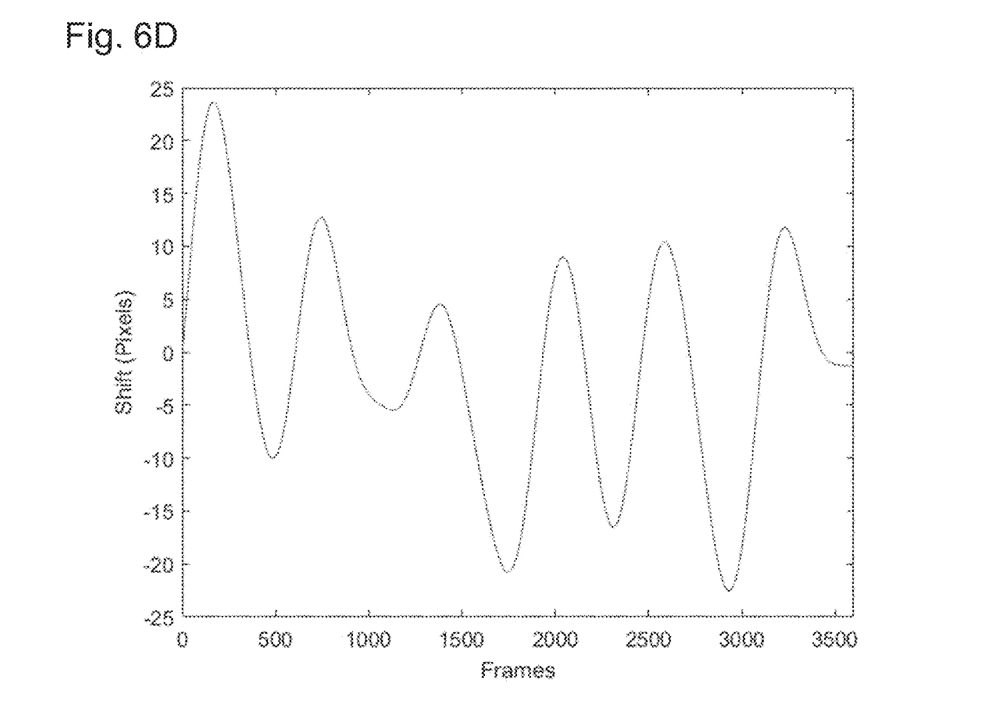
FIG. 6D shows the reconstructed shift curve after filtering.

Transforming the reconstructed shift curve into frequency domain (FIG. 6C), four peaks at 0.00833 Hz, 0.025 Hz, 0.05 HZ and 0.1 Hz were found with strong high-frequency components causing the noisy oscillation. The first and the second peak were treated as global artifacts because they just occurred one or two times through the whole recording. The second peak represented the highest peak which corresponds to the uterine contraction frequency, while the third peak could be the respiration frequency according to the literature [18]. A low-pass filter (LPF) may be applied to remove the high frequency oscillation and the respiration frequency. The cut-off frequency of this LPF was chosen as 0.0833 Hz to include the contraction rates produced by the most active uteri. The resulted shift curve after the LPF is shown in FIG. 6D.

The next step is to calculate the strain based on the tracking results.

C. Strain Calculation

Figure 7:
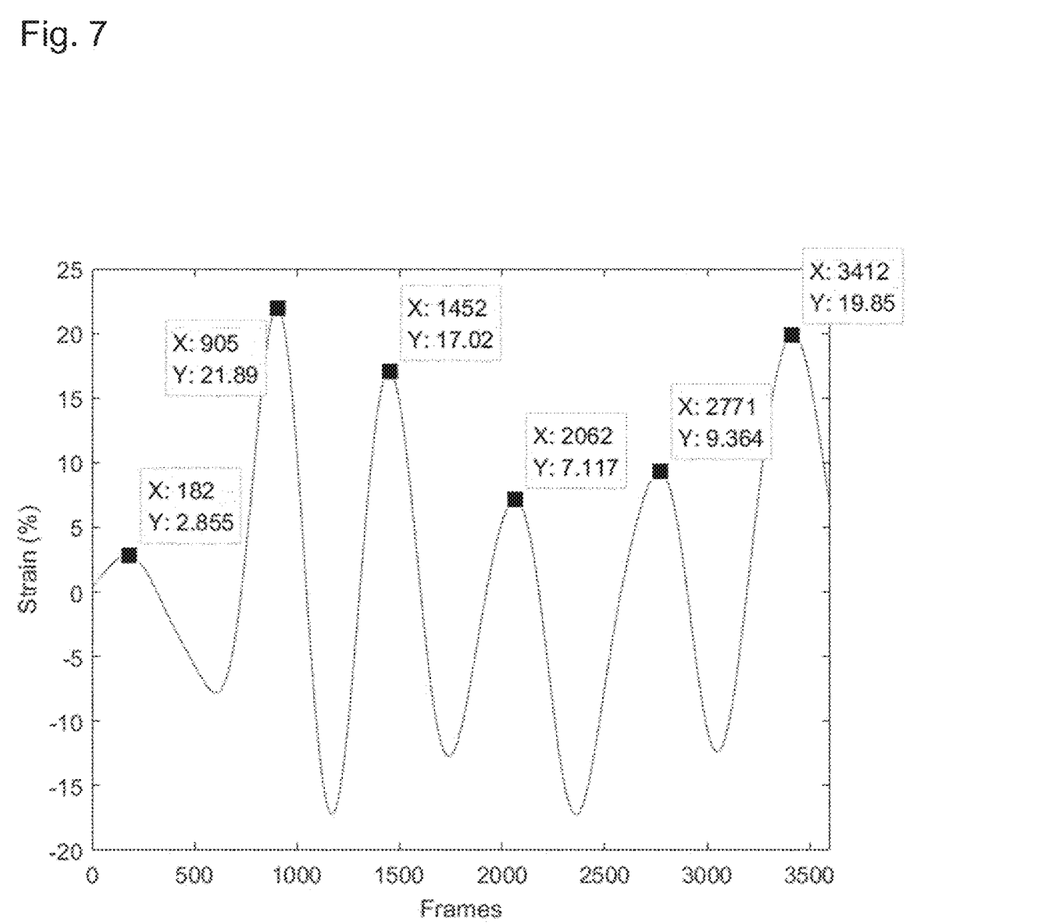
FIG. 7 shows a graph of area strain, consisted of four dots (Row 1 Column 5, Row 1 Column 6, Row 2 Column 5, Row 2 Column 6 in the dots-map (FIG. 1B)), after applying the LPF.

After calculating the strain based on the corresponding Eq. 1 and Eq. 2, the same LPF as in the previous section may be applied to obtain the results at desired frequency. FIG. 7 shows an example of the resulted area strain. A sinusoidal-alike wave with a period around 600 frames was successfully acquired (FIG. 7).

With the help of the interpolation and colour coding, the strain results are then translated into the coloured strain map.

Figure 8A:
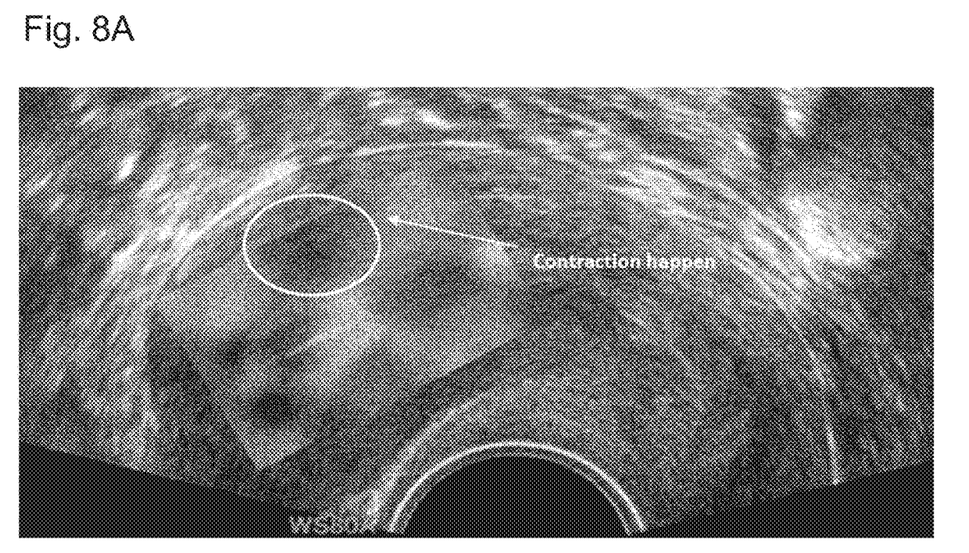
FIG. 8A is an example of an area strain map over TVUS recording (3'08") from the LF phase of the particular patient.
Figure 8B:
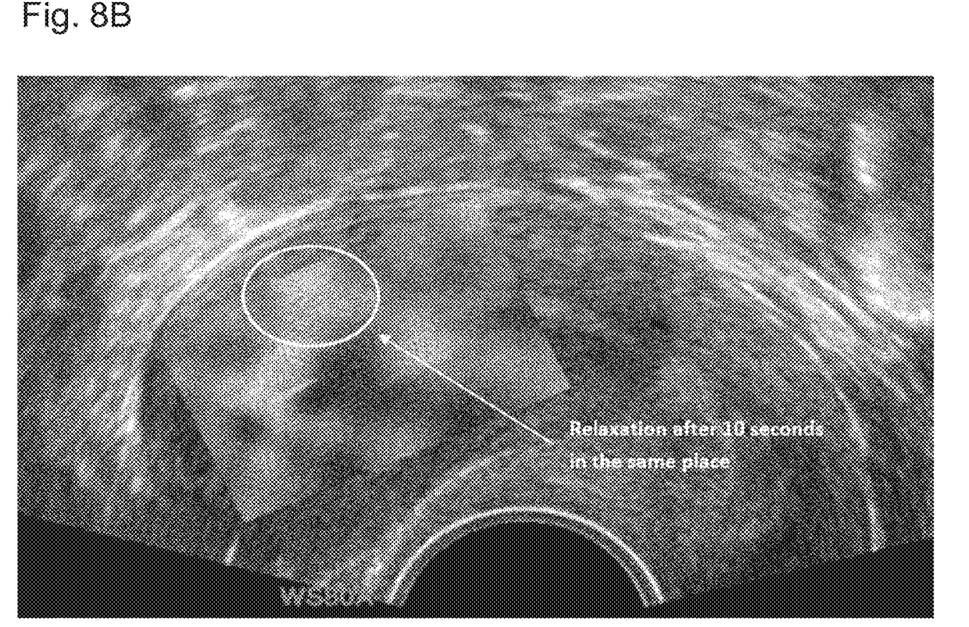
FIG. 8B is an example of an area strain map over TVUS recording (3'18") from the LF phase of the particular patient.

FIG. 8A shows one frame (3'08") of the TVUS recording from the LF phase of the particular patient with the area strain map. A contraction occurs in the out-lighted circle. After 10 seconds, the relaxation of the endometrium in this area was detected, see FIG. 8B which shows the relative variation in the areas determined by each 4 neighbouring (tracked) points. The results from the area strain maps agree with the contraction frequency reported in the literature for the LF phase [17]. By observing the video with the strain map, the changes in colour indeed follow the real motion of the uterus, confirming the reliability of the estimated strain.

Figure 9:
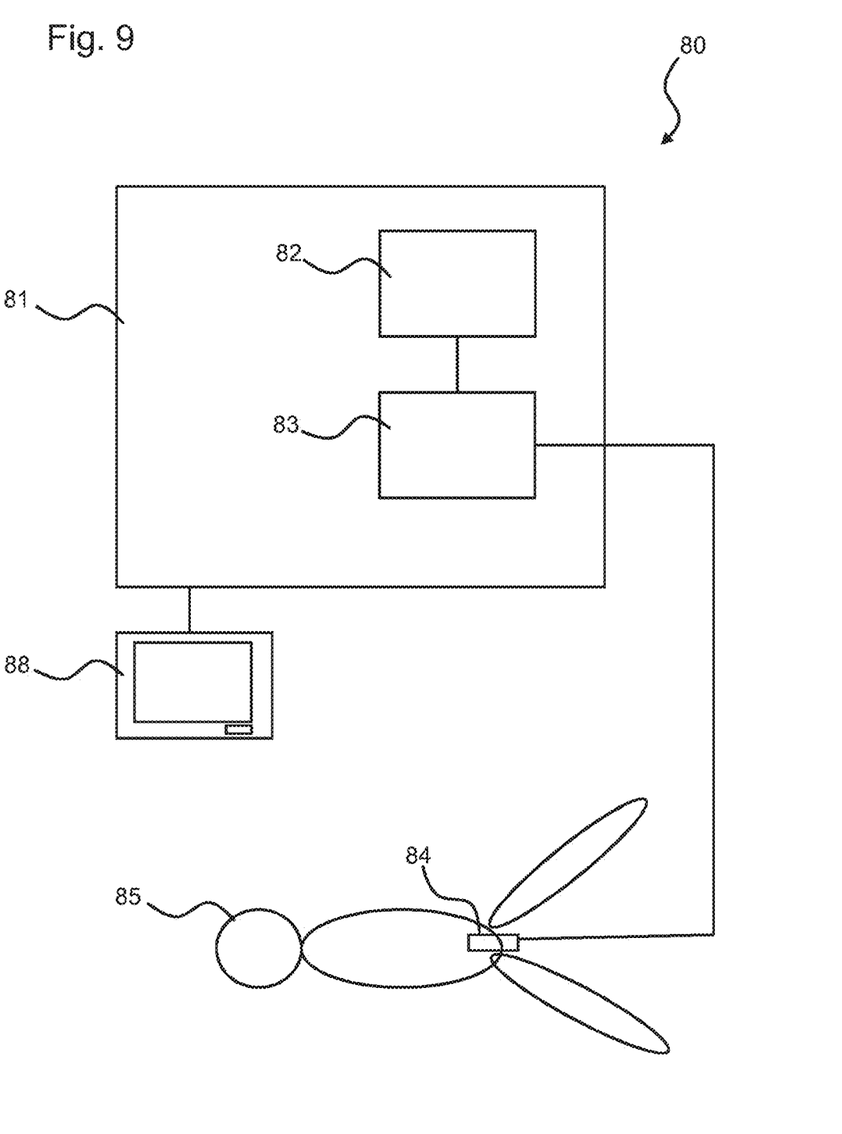
FIG. 9 schematically shows a system used to perform the method according to some embodiments of the presently disclosed subject matter.

FIG. 9 schematically shows a system 80 used to perform the method according to some embodiments of the presently disclosed subject matter. The system 80 includes a computer 81 having a processor 82 and an interface 83. The interface is arranged to receive measurement data from a measuring device 84, such as an ultrasound probe. The probe 84 is inserted into a patient or test person 85, although a transabdominal approach may also be considered. The system 80 may also include a display 88 for displaying the measured images and the calculated overlays. The processor 81 is arranged to execute instructions which may be stored on a computer readable medium such as an internal or external memory (not shown). These instructions will enable to make the processor 81 perform the method as described above.

Figure 10:
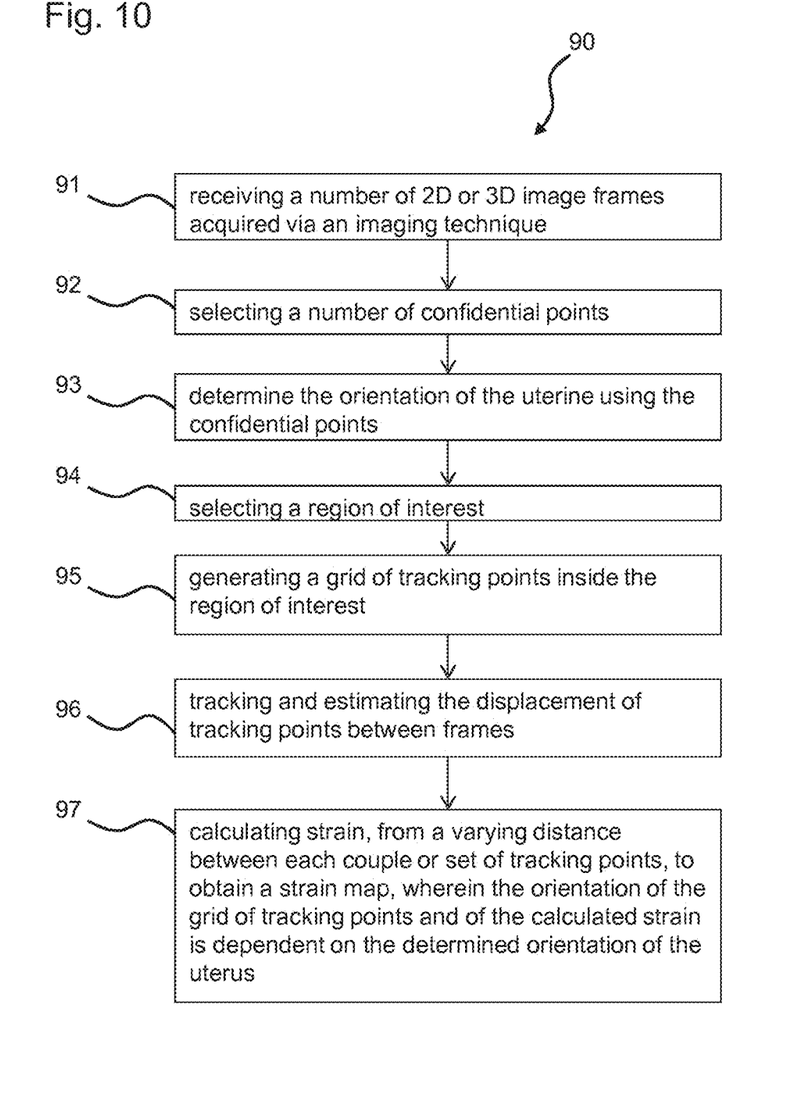
FIG. 10 shows a flow chart of the method according to some embodiments.

FIG. 10 shows a flow chart of a method 90 according to some embodiments of the presently disclosed subject matter. The method 90 starts with a step 91 of receiving a number of 2D or 3D image frames acquired via an imaging technique. A next step 92 represents the selecting a number of confidential points. A next step 93 represents the determining the orientation of the uterine using the confidential points. Then at step 94, a region of interest is selected. A next step 95 represents the generating a grid of tracking points inside the region of interest. A next step 96 represents the tracking and estimating the displacement of tracking points between frames. A next step 97 represents the calculating, from a varying distance between each couple or set of tracking points to obtain a strain map, wherein the orientation of the grid of tracking points and of the calculated strain is dependent on the determined orientation of the uterus.

It is noted that the strain, mentioned above, can be at least one of:
 a transversal strain,
 a longitudinal strain,
 a circular strain,
 an area strain and
 a volume strain.

Figure 11:
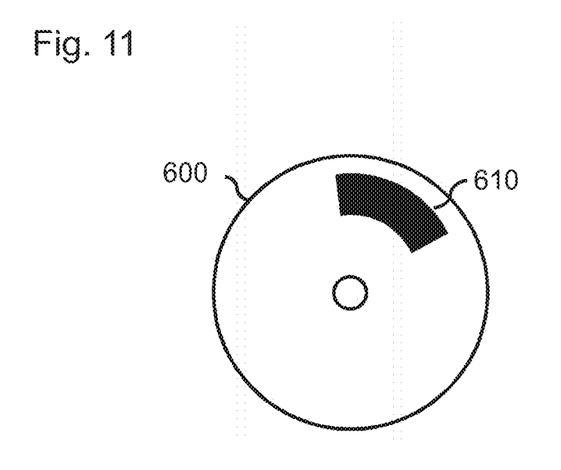
FIG. 11 shows a computer readable medium according to some other embodiments.

The method(s) may be implemented on a computer as a computer implemented method, as dedicated hardware, or as a combination of both. As also illustrated in FIG. 11, instructions for the computer, e.g., executable code, may be stored on a computer readable medium 600, e.g., in the form of a series 610 of machine readable physical marks and/or as a series of elements having different electrical, e.g., magnetic, or optical properties or values. The executable code may be stored in a transitory or non-transitory manner. Examples of computer readable mediums include memory devices, optical storage devices, integrated circuits, servers, online software, etc. FIG. 11 shows an optical disc 600. Alternatively, the computer readable medium 600 may include transitory or non-transitory data 610 representing metadata as described elsewhere in this specification.

There are two major challenges in future works. The first challenge is the interpretation of the UP with the strain mapping while the second is the tracking quality for 3D data. Several parameters, such as the threshold of the colour bar, the cut-off frequency of the LPF, and the window length of the MA filter, can be optimized after applying the strain mapping to all or most patients. These parameters were validated on the TVUS recordings of the LF phase of a particular patient. Statistical analysis might be used in the future to find the optimal thresholds and parameters. Therefore, additional validation on healthy women as well as on more phases of the menstrual cycle is advisable to prove the clinical value of this method. Meanwhile, it will be interesting and helpful to evaluate whether the difference between the LF and LL phases can be distinguished by the strain results. Moreover, the interpretation of the UP now is achieved by showing different colours in the ROI. However, sometimes the changes are too fast or too slow, complicating the interpretation in terms of contraction and relaxation. Additional options, such as adding alarms (beeps or beams) when contractions are detected, testing segmented strain mapping or generating strain-rate maps to study the strain evolution over time, might also contribute to a better understanding. Additional features may include the visualization of the phase velocity vector (amplitude and direction) of the estimated contraction/relaxation waves, which could be visualized with arrows overlaid on the images as well as with dedicated colour maps. Eventually, the obtained strain estimates should also be evaluated for their support with the prediction of successful embryo implantation following in-vitro fertilization procedures.

The tracking quality can represent a problem for 3D analysis due to several reasons. The first one refers to the lower volume rate (1 Hz) compared to 2D (30 Hz). Some movements of the uterus may be faster than Nyquist limit, leading to aliasing and misinterpretation of the recorded tissue movement. On the other hand, since the uterine contraction frequency is around 0.05 Hz, which is still lower than half of the sampling frequency, correct reconstruction of UP should remain feasible.

The second reason refers to the pre-processing steps. Substantially all pre-processing steps being applied in 2D need to be extended into 3D. New problems might occur in this progress, such as the up sampling that is facing a limitation of the RAM storage. To up sample a 600 by 600 by 600 volume by a factor of 2, it is needed more than 11 GB RAM during the operation. The size of the file after up sampling is very large, reading and writing such a large matrix may require long computation time. Yet, there are several approaches such as using GPUs for parallel computation or more efficient programming which might help to solve the computation problem.

After the tracking quality in 3D is validated by the use of the dedicated ex-vivo set up developed in our group, implementation of 3D volumetric strain will be performed. Since it is difficult to create a 4D strain mapping video, the preliminary idea is to display the strain map in sagittal, transversal and coronal planes at the same time, but with dynamic slices and time axis. These planes can be defined either relative to the patient or relative to the uterus, enabling us to estimate and visualize strain in the longitudinal, radial, and circular (about the longitudinal axis of the uterus) direction.

Successful In-Vitro Fertilization (IVF) is achieved in 30% of the procedures. Implantation failure can possibly be caused by dysfunction of the uterine peristalsis (UP). The IVF success rate can therefore be improved by novel methods enabling objective and non-invasive characterization of UP. In the embodiments described above, strain mapping based on speckle tracking was applied on two-dimensional (2D) transvaginal ultrasound (TVUS) video loops to quantify UP outside pregnancy. Six healthy women, with a natural regular cycle, underwent 4-minute TVUS during late follicular (LF) and late luteal (LL) phase, suggested to be the most active and the quietest phase of the menstrual cycle, respectively. Region Of Interest (ROI) was chosen to include the junctional zone close to the fundus. Strain mapping may be applied to calculate and visualize strain variations in the ROIs. We considered contraction as negative strain and relaxation as positive strain. The obtained strain maps were rendered with a suitable color map; red color for relaxation and blue color for contraction. For each recording, different strain maps, including longitudinal strain map, transversal strain map and area strain map, were created in order to visualize UP in different directions and dimensions.

Instead of using 2D images, one could use 3D images. Three-dimensional (3D) TVUS video loops may be analyzed based on 3D speckle tracking method. 3D analysis will allow a better understanding about natural UP along the three dimensions, without out-of-plane motion problem. A volumetric strain map, representing the relative volume change among adjacent dots, can then be created.

It should be noted that the above-mentioned embodiments illustrate rather than limit the presently disclosed subject matter, and that those of ordinary skill in the art will be able to design many alternative embodiments.

In the claims, any reference signs placed between parentheses shall not be construed as limiting the claim. Use of the verb "include" and its conjugations does not exclude the presence of elements or steps other than those stated in a claim. The article "a" or "an" preceding an element does not exclude the presence of a plurality of such elements. The presently disclosed subject matter may be implemented by hardware including several distinct elements, and by a suitably programmed computer. In the device claim enumerating several elements, several of these elements may be embodied by one and the same item of hardware. The mere fact that certain measures are recited in mutually different dependent claims does not indicate that a combination of these measures cannot be used to advantage.

REFERENCES

[1] G. F. Whitman-Elia and E. G. Baxley, "A primary care approach to the infertile couple" The Journal of the American Board of Family Practice, vol. 14, no. 1, pp. 33-45, 2001.
[2] A. N. Andersen, V. Goossens, A. P. Ferraretti, S. Bhattacharya, R. Felberbaum, J. de Mouzon, and K. G. Nygren, "Assisted reproductive technology in europe, 2004: results generated from european registers by eshre" Human reproduction (Oxford, England), vol. 23, no. 4, pp. 756-771, 2008.
[3] R. Fanchin and J. M. Ayoubi, "Uterine dynamics: impact on the human reproduction process" Reprod Biomed Online, vol. 18 Suppl 2, pp. 57-62, 2009.
[4] R. Fanchin, C. Righini, F. Olivennes, S. Taylor, D. de Ziegler, and R. Frydman, "Uterine contractions at the time of embryo transfer alter pregnancy rates after in-vitro fertilization" Hum Reprod, vol. 13, no. 7, pp. 1968-74, 1998.
[5] M. M. Ijland, H. J. Hoogland, G. A. Dunselman, C. R. Lo, and J. L. Evers, "Endometrial wave direction switch and the outcome of in vitro fertilization" Fertil Steril, vol. 71, no. 3, pp. 476-81, 1999.
[6] T. Kawagishi. Speckle tracking for assessment of cardiac motion and dyssynchrony. Echography, 25(10):116771, 2008.
[7] R. G. P. Lopata, J. P. van Dijk, S. Pillen, M. M. Nillesen, H. Maas, J. M. Thijssen, D. F. Stegeman, and C. L. de Korte. Dynamic imaging of skeletal muscle contraction in three orthogonal directions. Journal of Applied Physiology, 109(3):906915, 1986.
[8] Novellas S, Chassang M, Delotte J, et al. MRI characteristics of the uterine junctional zone: from normal to the diagnosis of adenomyosis[J]. American Journal of Roentgenology, 2011, 196(5): 1206-1213.
[9] M. Mischi, N. P. M. Kuijsters, F. Sammali, C. Rabotti, and B. C. Schoot, "Feasibility of uterine speckle tracking for improved embryo implantation" Ultrasonics Symposium (IUS), 2015 IEEE International, 2015
[10] IJland M M, Evers J L H, Hoogland H J. Velocity of endometrial wavelike activity in spontaneous cycles[J]. Fertility and sterility, 1997, 68(1): 72-75.
[11] Mischi M, Rabotti C, Kuijsters N, et al. Quantitative ultrasound imaging of the uterus for improved embryo implantation: Preliminary study[C]//Digital Signal Processing (DSP), 2015 IEEE International Conference on. IEEE, 2015: 274-277.
[12] Kaur A, Kaur A. Transvaginal ultrasonography in first trimester of pregnancy and its comparison with transabdominal ultrasonography[J]. Journal of Pharmacy and Bioallied Sciences, 2011, 3(3): 329.
[13] Vanne J, Aho E, Hamalainen T D, et al. A high-performance sum of absolute difference implementation for motion estimation[J]. IEEE Transactions on Circuits and Systems for Video Technology, 2006, 16(7): 876-883.
[14] Barjatya A. Block matching algorithms for motion estimation[J]. IEEE Transactions Evolution Computation, 2004, 8(3): 225-239.
[15] Shan Zhu, and Kai-Kuang Ma, "A New Diamond Search Algorithm for Fast Block-Matching Motion Estimation", IEEE Trans. Image Processing, vol 9, no. 2, pp. 287-290, February 2000.
[16] Chi-Wai Lam, Lai-Man Po and Chun Ho Cheung, "A new cross-diamond search algorithm for fast block matching motion estimation", Neural Networks and Signal Processing, 2003, December 2003 [17] Kuijsters N P M, Methorst W G, Kortenhorst M S Q, Rabotti C, Mischi M, Schoot B C, "Uterine peristalsis and fertility: current knowledge and future perspectives: a review and meta-analysis", Reproductive BioMedicine Online, Volume 35, Issue 1, 50-71, table 1
[18] Barrett K, Brooks H, Boitano S, Barman S, Ganong's Review of Medical Physiology (24 ed.). p. 619. ISBN 0071780033.
[19] Huang, Sheng-Wen, et al. "Analysis of correlation coefficient filtering in elasticity imaging." IEEE transactions on ultrasonics, ferroelectrics, and frequency control 55.11 (2008).
[20] Mailloux, Guy E., et al. "Computer analysis of heart motion from two-dimensional echocardiograms." IEEE Transactions on Biomedical Engineering 5 (1987): 356-364.

The invention claimed is:

1. A method for quantitative visualization of uterine strain, the method comprising:
receiving a number of 2D or 3D image frames acquired via an imaging technique;
selecting a number of confidential points;
determining the orientation of the uterine using the confidential points;
selecting a region of interest;
generating a grid of tracking points inside the region of interest;
tracking and estimating the displacement of tracking points between frames; and
calculating, from a varying distance between each couple or set of tracking points, at least one of:
a transversal strain,
a longitudinal strain,
a circular strain,
an area strain, and
a volume strain,
to obtain a strain map, wherein the orientation of the grid of tracking points and of the calculated strain is dependent on the determined orientation of the uterus.

2. The method according to claim 1 further comprising:
visualizing the 2D or 3D image frames with their corresponding strain map as an overlay.

3. The method according to claim 2 further comprising:
rendering the obtained strain map with a predefined color map to present a colored strain map for each frame in time; and
visualizing the 2D or 3D image frames with the colored strain maps as an overlay.

4. The method according to claim 1, wherein a bull eye plot is used to visualize 3D strain where the center of the plot represents strain in the cervix and the outer ring represents strain in the fundus or vice versa.

5. The method according to claim 1, wherein the area strain is determined based on the changes in the areas determined by sets of 3 or more of the tracking points, where the points are positionable relative to the uterine anatomy.

6. The method according to claim 1, wherein the tracking comprises optical flow techniques.

7. The method according to claim 1, wherein the tracking comprises block matching.

8. The method according to claim 7, wherein the block matching comprises:
- preprocessing of the images by regularization, filtering, or decomposition methods;
- defining one or more blocks in a frame;
- defining a similarity measure, such as normalized correlation, mutual information, or sum of absolute errors;
- searching for the most similar blocks in the following frame;
- using smart search algorithms, such as a diamond search;
- combining the displacement estimates from neighboring blocks, using median or average filters;
- summing the estimated displacements over time; and
- post processing, such as moving average filtering.

9. The method according to claim 1, wherein the strain is at least one of: the transversal strain, the longitudinal strain, the circular strain and the area strain, and calculated in directions relative to the endometrial long axis and presented in radial, longitudinal, and circular directions.

10. The method according to claim 1, wherein the strain is at least one of: the transversal strain, the longitudinal strain, the circular strain and the area strain, and calculated in directions relative to the outer contour of the uterus or the endometrium and presented in radial, longitudinal, and circular directions.

11. The method according to claim 1, wherein the calculated strain map is projected on one or more 2D images for presentation purposes.

12. The method according to claim 11, wherein the presented dynamic map of strain is accelerated for visualization purposes.

13. The method according to claim 1, wherein a global uterine activity parameter is provided for quantification of the strain amplitude, strain direction, and/or frequency spectrum of the strain.

14. The method according to claim 1, wherein contractions in the uterus are counted based on changes in either direction or amplitude of strain, or both.

15. The method according to claim 14 further comprising:
- calculating a propagation velocity and a direction of the uterine contractions relative to the orientation of the uterus using the measured contractions.

16. The method according to claim 1, wherein the step of selecting a number of confidential points comprises receiving orientation information on the orientation and/or outline of the uterine from a user.

17. The method according to claim 1, wherein the imaging technique is an ultrasound imaging technique, and the frames consist of either a set of Radio-frequency lines or demodulated gray-level images.

18. A system for quantitative visualization of uterine strain, the system comprising a computer having a processor and an interface, the interface being arranged to receive measurement data from a measuring device, wherein the processor is arranged to perform the method according to claim 1.

19. A non-transitory computer readable storage medium for storing a computer program comprising instructions which when executed by a computer cause the computer to perform the method according to claim 1.

* * * * *